(12) United States Patent
Yamamoto

(10) Patent No.: US 9,961,930 B2
(45) Date of Patent: May 8, 2018

(54) KOJI FERMENTED COMPOSITION, SEASONING USING THE SAME, ANTIOXIDANT, AND FOOD OR BEVERAGE

(71) Applicant: KIRISHIMA HIGHLAND BEER CO., LTD., Kagoshima (JP)

(72) Inventor: Masahiro Yamamoto, Kagoshima (JP)

(73) Assignee: Kirishima Highland Beer Co., Ltd., Kagoshima (JP)

( * ) Notice: Subject to any disclaimer, the term of this patent is extended or adjusted under 35 U.S.C. 154(b) by 70 days.

(21) Appl. No.: 15/107,945

(22) PCT Filed: Jan. 29, 2015

(86) PCT No.: PCT/JP2015/052513
§ 371 (c)(1),
(2) Date: Jun. 24, 2016

(87) PCT Pub. No.: WO2015/119036
PCT Pub. Date: Aug. 13, 2015

(65) Prior Publication Data
US 2016/0309760 A1    Oct. 27, 2016

(30) Foreign Application Priority Data
Feb. 10, 2014    (JP) .................................. 2014-023263

(51) Int. Cl.
*A23B 7/10*      (2006.01)
*C12N 1/14*      (2006.01)
*A23L 27/24*     (2016.01)

(52) U.S. Cl.
CPC ................ *A23L 27/24* (2016.08); *C12N 1/14* (2013.01); *A23V 2002/00* (2013.01)

(58) Field of Classification Search
CPC .................................. A23L 27/24; C12N 1/14
USPC ........................................................... 426/52
See application file for complete search history.

(56) References Cited

U.S. PATENT DOCUMENTS 3,852,479 A * 12/1974 Yokotsuka ................ A23J 3/34
426/44
2005/0202123 A1    9/2005 Fujita et al.
2012/0220650 A1    8/2012 Yanagita et al.

FOREIGN PATENT DOCUMENTS

| JP | 05-344852   | 12/1993 |
| JP | 2005-278519 | 10/2005 |
| JP | 2008-263831 | 11/2008 |
| JP | 2009-028010 | 2/2009  |
| JP | 2011-083280 | 4/2011  |
| JP | 2012-080812 | 4/2012  |
| JP | 5039984     | 10/2012 |

(Continued)

OTHER PUBLICATIONS

Smith et al. 1991. Biotechnol. Bioeng. Abstract (Year: 1991).*

(Continued)

*Primary Examiner* — Hamid R Badr
(74) *Attorney, Agent, or Firm* — Haug Partners LLP; William S. Frommer

(57) ABSTRACT

Provided are: a koji fermented composition that, when using black koji fungus, has a reduced amount of generated citric acid without a loss in xylanase activity or acid protease activity of the black koji fungus; and a method for producing the koji fermented composition. The koji fermented composition is obtained by contacting tea leaves to black koji fungus, and culturing the result.

2 Claims, 6 Drawing Sheets

(56) References Cited

FOREIGN PATENT DOCUMENTS

JP          2013-255522       12/2013
WO      Wo2015/119036        8/2015

OTHER PUBLICATIONS

JP-2012-219077—Machine Translation. (Year: 2012).*
International Search Reportissued in corresponding International Application No. PCT/JP2015/052513 dated May 19, 2014.
Chika Orii, "Kin ga Tsukuru Oclaa no Kagaku",*Journal of the Society for Bioscience and Bioengineering*, Japan, 2010, vol. 88, No. 9, p. 489.
Hong SB. et al., Aspergillus luchuensis, an industrially important black Aspergillus in East Asia., *PLoS* (online), vol. 8, No. 5, 2013, E63769, http://www.ncbi.nlm.nih.gov/pmc/artieles/PMC3665839/pdf/pone.0063769.pdf.
Lo'pez JA. et al., Characterization of multienzyme solutions produced by solidstate fermentation of babassu cake, for use in cold hydrolysis of raw biomass., *Biochemical Engineering Journal*, 2013, vol. 77, pp. 231-239.
Written Opinion issued in corresponding International Application No. PCT/JP2015/052513, dated May 19, 2015.
IPO of Singaport Search Report dated Nov. 18, 2016.
IPO of Singapore Written Opinion dated Feb. 9, 2017.

* cited by examiner

[Figure 1]
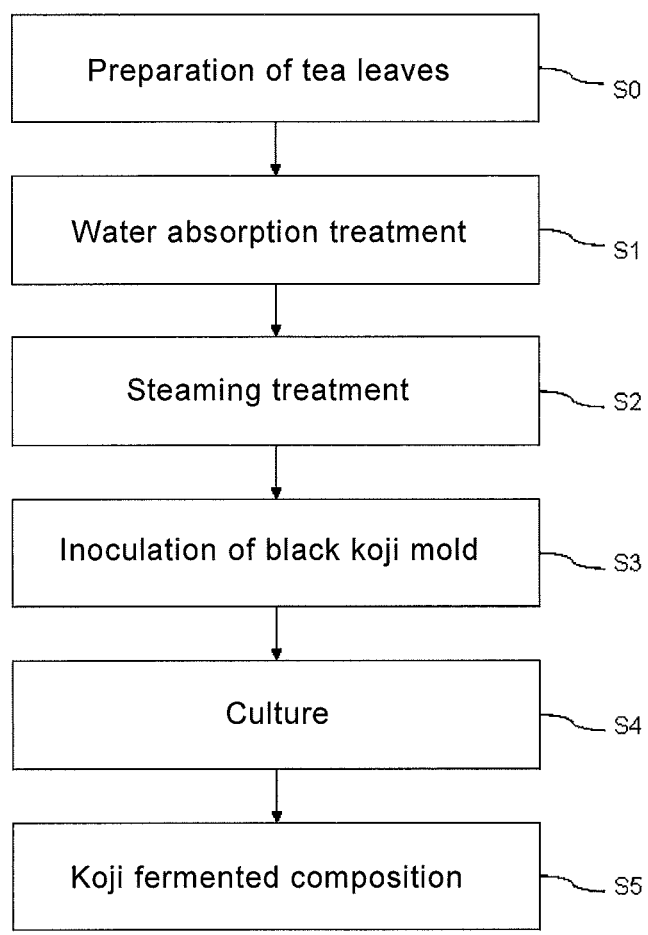

[Figure 2a]
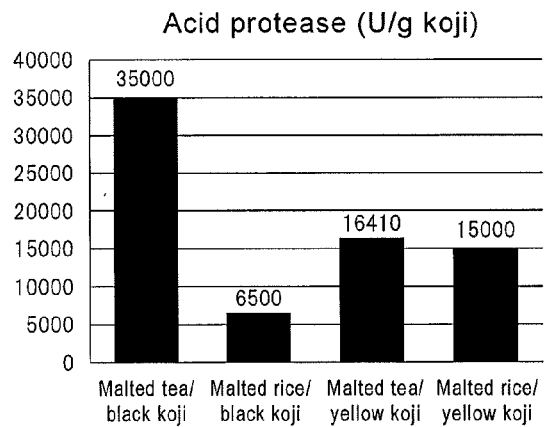
[Figure 2b]
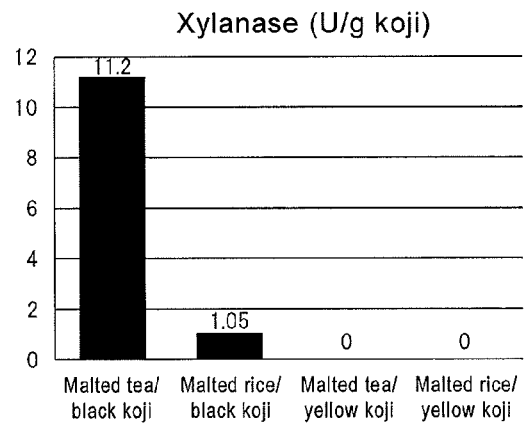
[Figure 2c]
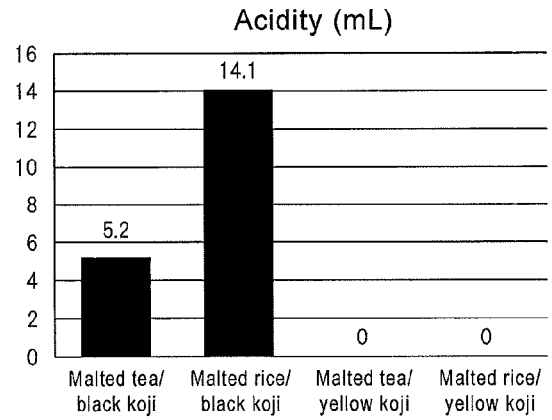

[Figure 3]
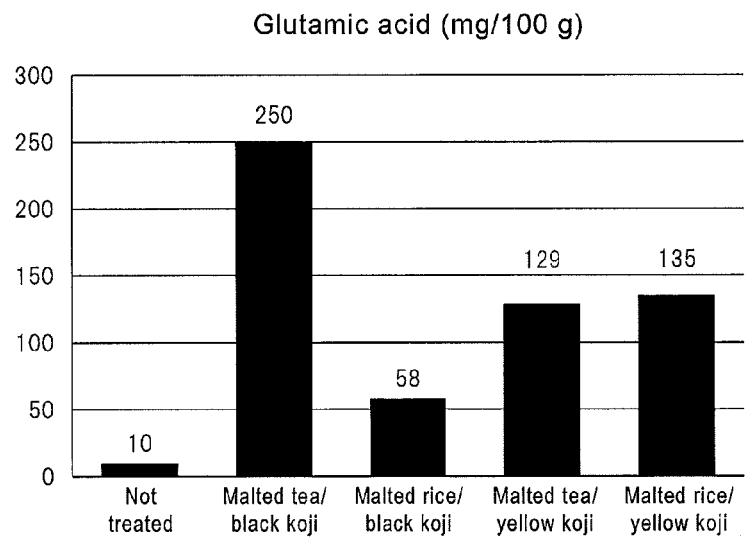
[Figure 4]
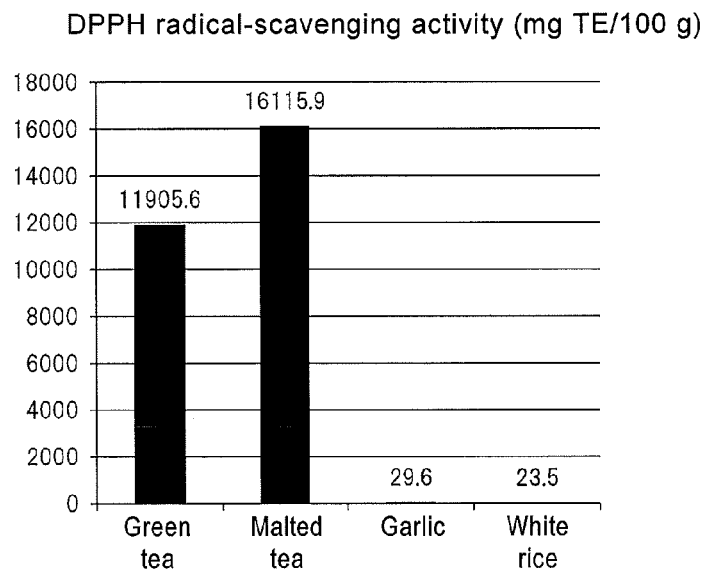

[Figure 5]
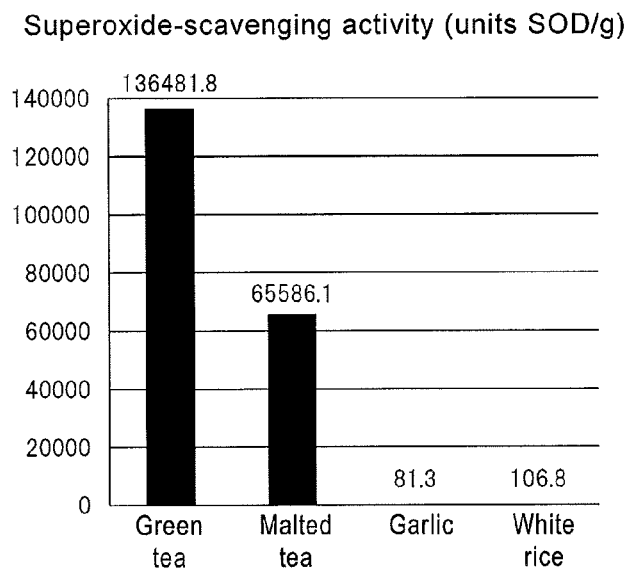
[Figure 6]
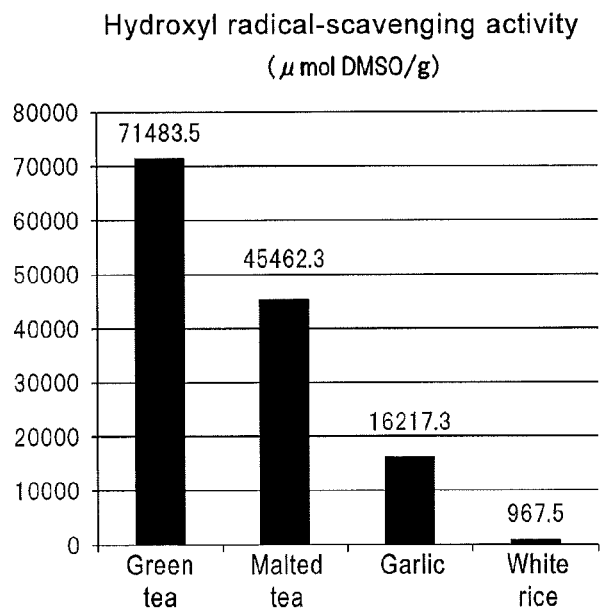

[Figure 7]
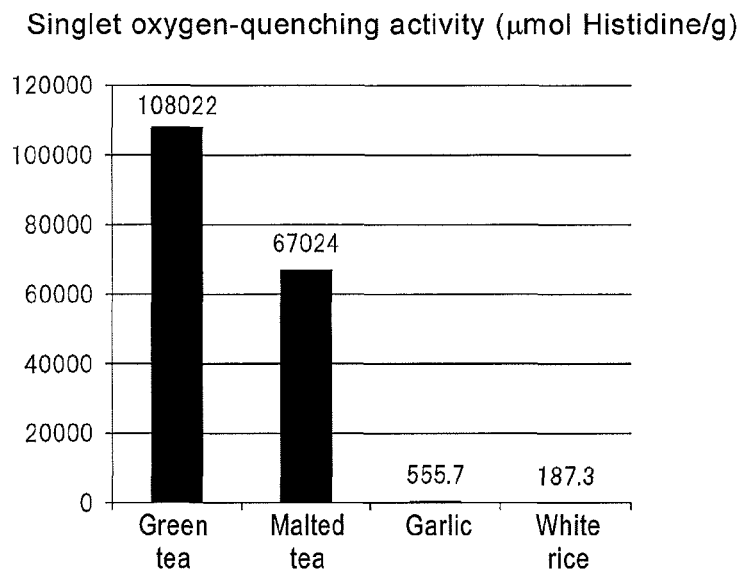
[Figure 8]
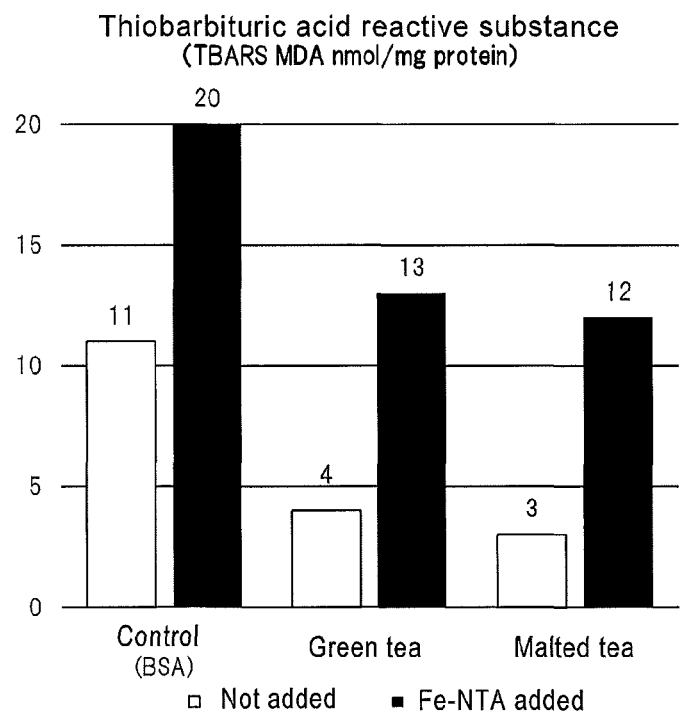

[Figure 9]
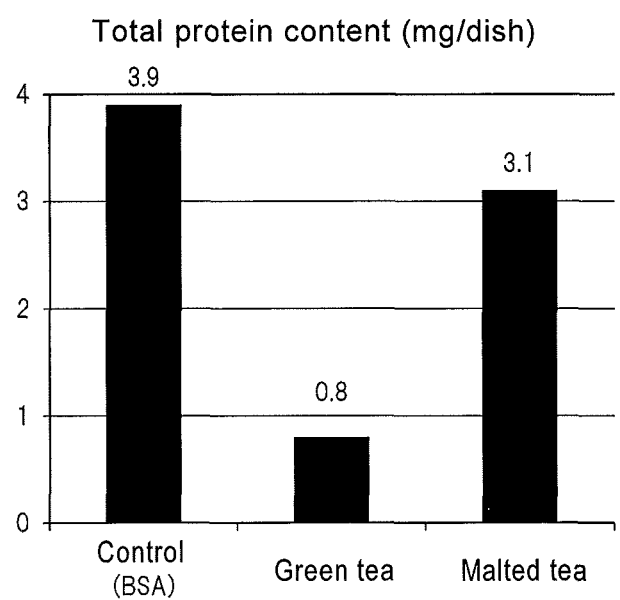

KOJI FERMENTED COMPOSITION, SEASONING USING THE SAME, ANTIOXIDANT, AND FOOD OR BEVERAGE

TECHNICAL FIELD

The present invention relates to a koji fermented composition obtained by fermenting tea leaves with black koji mold such as *Aspergillus awamori*, and a seasoning, an antioxidant, and a food product or beverage, in which this composition is used.

BACKGROUND ART

In recent years, traditional Japanese koji-fermented food products using koji have been re-evaluated and become popular. "Koji" means a product obtained by steaming rice, wheat, bean or the like, and then allowing koji mold to proliferate therein. Among them, koji obtained by allowing koji mold to proliferate in rice is referred to as "rice koji (malted rice)". The malted rice is mainly used in the production of fermented food products such as sake (rice wine), soy sauce, miso (fermented bean paste), or amazake (sweet fermented rice drink). In addition, the malted rice is also used as a seasoning. Koji mold contained in this malted rice has an ability to produce many types of enzymes such as protease or amylase. Accordingly, such malted rice is added to or sprinkled on a food material such as meat, fish or vegetables to degrade ingredients contained in the food material, so that the food material itself can be softened, or a natural sweet taste or umami (good taste) can be given to the food material. As such koji mold used for the malted rice, yellow koji mold such as *Aspergillus oryzae* has been mostly used, as described in Patent Literature 1.

On the other hand, black koji mold is another koji mold. As in the case of other koji molds, the black koji mold is characterized in that it produces many types of enzymes such as protease or amylase. However, the black koji mold is characterized in that it produces a large amount of citric acid. The black koji mold is mainly used in the production of distilled spirits such as *Awamori*. Accordingly, regarding the black koji mold, studies have been mainly conducted, focusing on the enhancement of the enzyme activity of amylase to glycosylate starch contained in raw materials so as to improve the efficiency of production of distilled spirits, as described in Patent Literature 2.

CITATION LIST

Patent Literature

[Patent Literature 1] Japanese Patent Laid-Open No. 2013-106598
[Patent Literature 2] Japanese Patent No. 4083194

SUMMARY OF INVENTION

Technical Problem

As described above, black koji mold produces a large amount of citric acid. Therefore, acid protease produced by the black koji mold is able to retain its activity even in a highly acidic environment. As such, by using black koji mold as koji mold, koji or a koji-fermented food product, which comprises the function of retaining its activity, for example, even in stomach and promoting digestion of foods, can be obtained. Moreover, the black koji mold also produces xylanase degrading the cell wall of plants. Thus, by using koji obtained by the black koji mold to plant food materials such as vegetables or fruits, the effect of eluting an umami ingredient inside of the cell of the plant food materials, the effect of softening the plant food materials, etc. can also be obtained.

However, the malted rice obtained by the black koji mold as koji mold has been problematic in that the malted rice has a strong acid taste, which is caused by citric acid produced by the black koji mold, and thus, in that the malted rice gives an acid taste to a food material, when it is used for the food material as a seasoning.

The present invention has been made in consideration of the aforementioned point. It is an object of the present invention to provide a koji fermented composition, which is produced using black koji mold as koji mold, and in which the amount of citric acid generated is reduced, without losing acid protease activity or xylanase activity produced by the black koji mold, and a method for producing the koji fermented composition.

Moreover, it is another object of the present invention to discover another activity or function of the above described koji fermented composition and to provide a novel intended use thereof.

Solution to Problem

The koji fermented composition of the present invention, which achieves the aforementioned objects, is obtained by inoculating black koji mold into tea leaves, and culturing the tea leaves. By using tea leaves as raw materials and allowing black koji mold to proliferate in the tea leaves, a koji fermented composition, in which the amount of citric acid generated is reduced to less than half in the case of malted rice using rice as a raw material and in which the acid protease activity and xylanase activity are enhanced, can be obtained. Hence, in a case where the koji fermented composition of the present invention is used for food products, or is further subjected to a fermentative treatment to produce a koji-fermented food product, a food product having a low acid taste and high activities of the above described enzymes can be obtained. In particular, since the protease possessed by the koji fermented composition of the present invention is able to maintain its activity even under strongly acidic conditions, the present koji fermented composition is able to promote the decomposition of proteins, for example, in a low pH environment such as the inside of the stomach. In addition, the koji fermented composition of the present invention has a high antioxidative activity, and its cell growth inhibitory activity is low. Accordingly, the present koji fermented composition can be used as a highly safe antioxidant in the fields of food products, medicines, cosmetics, etc.

Moreover, with regard to the koji fermented composition of the present invention, the above described black koji mold is preferably inoculated into steamed tea leaves. Thereby, bacteria in the tea leaves are sterilized, and also, oxidase contained in the tea leaves is inactivated, so that black koji mold is allowed to efficiently proliferate in the tea leaves, thereby obtaining a koji fermented composition in a short time.

Furthermore, in the koji fermented composition of the present invention, the black koji mold is preferably at least one selected from the group consisting of *Aspergillus awamori*, *Aspergillus luchuensis*, and *Aspergillus inuii*.

Thereby, a preferred mold species can be selected as a black koji mold for obtaining the koji fermented composition of the present invention.

Further, the seasoning of the present invention contains the above described koji fermented composition or an extract thereof. As described above, in the koji fermented composition of the present invention, the amount of citric acid generated is reduced to less than half in comparison to malted rice using rice as a raw material, and the acid protease activity and xylanase activity are enhanced. Hence, by using the koji fermented composition or an extract thereof having such a property as a seasoning, ingredients contained in a food material are degraded by enzymes contained in the koji fermented composition, and a natural sweet taste or umami can be added to the food material. In addition, by this enzymatic decomposition action, the food material itself can be softened. At this time, since the amount of citric acid generated in the koji fermented composition of the present invention can be reduced, an acid taste caused by the citric acid hardly affects the taste of the food material.

Further, the antioxidant of the present invention contains the above described koji fermented composition or an extract of the koji fermented composition. The koji fermented composition of the present invention has an antioxidative activity of suppressing lipid peroxidation and removing active oxygen. Thus, the koji fermented composition or an extract thereof can be used as an antioxidant. In addition, since this koji fermented composition has a low cell growth inhibitory activity and is further derived from a food product, it can be used as a highly safe antioxidant.

Further, the food product or beverage of the present invention contains the above described koji fermented composition or an extract thereof. This koji fermented composition contains protease that is able to maintain its activity even under strongly acidic conditions, and thus, the present koji fermented composition is able to promote the decomposition of proteins even in a strict pH environment such as the inside of the stomach. In addition, since this koji fermented composition also has an antioxidative activity of suppressing active oxygen reactions or lipid peroxidation reactions, which are associated with the mechanisms of various diseases, it can be used as an active ingredient of medicines or functional foods.

Still further, the method for enhancing the umami of a food material of the present invention comprises a step of adding the above described koji fermented composition or an extract thereof to a food material. By applying the koji fermented composition of the present invention or an extract thereof to a food material, ingredients contained in the food material are degraded by enzymes contained in the koji fermented composition, and a sweet taste or umami can be added to the food material. In particular, since acid protease activity is enhanced in the koji fermented composition of the present invention, proteins contained in the food material are degraded well, and amino acids constituting umami ingredients such as glutamic acid can be obtained. In addition, since xylanase activity is also enhanced in the koji fermented composition of the present invention, cell walls in plant food materials comprising hemicellulose as a main ingredient are easily degraded, and as a result, sweet tastes or umami ingredients can be eluted from inside of the cell walls. As such, by coating or putting the koji fermented composition of the present invention or an extract thereof on a food material, the umami taste of the food material can be easily increased, and thus, the food material can be processed to have a delicious taste.

Still further, the method for producing a koji fermented composition having a reduced amount of citric acid generated and enhanced protease activity and xylanase activity of the present invention comprises a step of inoculating black koji mold into tea leaves and a step of culturing the tea leaves. By using tea leaves as main raw materials, inoculating black koji mold into the tea leaves, and then culturing the tea leaves to allow the black koji mold to proliferate therein, koji, in which the amount of citric acid generated is small and the acid protease activity and xylanase activity are improved, can be obtained.

Still further, in the above described method for producing a koji fermented composition of the present invention, the black koji mold is preferably at least one selected from the group consisting of *Aspergillus awamori*, *Aspergillus luchuensis*, and *Aspergillus inuii*.

Advantageous Effects of Invention

According to the present invention, a koji fermented composition having the following excellent effects can be provided.
(1) A koji fermented composition, in which the amount of citric acid generated is small and the acid protease activity and xylanase activity are enhanced in comparison to rice koji (malted rice), can be obtained.
(2) Since protease contained in the koji fermented composition maintains its activity even under strongly acidic conditions, it contributes to stimulate digestion of foods in the stomach.
(3) By adding the koji fermented composition to a food material, enzymes contained in the koji fermented composition efficiently degrade ingredients contained in the food material, and a natural sweet taste or umami can be easily added to the food material. Moreover, by the enzymatic decomposition, the food material itself can be softened.
(4) Since the koji fermented composition has an action to suppress lipid peroxidation and remove active oxygen, namely, an antioxidative activity, it can be used as an active ingredient of antioxidants, medicines or functional foods. Moreover, since this koji fermented composition has a low cell growth inhibitory activity and is derived from a food product, it is highly safe.

BRIEF DESCRIPTION OF DRAWINGS

FIG. 1 is a flow chart schematically showing the method for producing a koji fermented composition according to the embodiment of the present invention.

FIG. 2a is a graph showing the results obtained by measuring the acid protease activity of each koji fermented composition in Example 2.

FIG. 2b is a graph showing the results obtained by measuring the xylanase activity of each koji fermented composition in Example 2.

FIG. 2c is a graph showing acidity of each koji fermented composition in Example 2.

FIG. 3 is a graph showing the results obtained by measuring the amount of free glutamic acid in a pork meat treated with each koji fermented composition in Example 3.

FIG. 4 is a graph showing the DPPH radical-scavenging activities of the koji fermented composition of the present invention and other food products in Example 4.

FIG. 5 is a graph showing the superoxide anion radical-scavenging activities of the koji fermented composition of the present invention and other food products in Example 4.

FIG. 6 is a graph showing the hydroxyl radical-scavenging activities of the koji fermented composition of the present invention and other food products in Example 4.

FIG. 7 is a graph showing the singlet oxygen-quenching activities of the koji fermented composition of the present invention and other food products in Example 4.

FIG. 8 is a graph showing the antioxidative activities of the koji fermented composition of the present invention, green tea as a raw material thereof, and a control (BSA), which are shown in terms of TBARS concentrations in Example 5.

FIG. 9 is a graph showing the cell growth inhibitory actions of the koji fermented composition of the present invention, green tea as a raw material thereof, and a control (BSA), which are shown in terms of total protein contents in cells in Example 5.

DESCRIPTION OF EMBODIMENTS

First of all, with reference to FIG. 1, the method for producing a koji fermented composition of the present invention will be described.

As shown in FIG. 1, the method for producing a koji fermented composition according to the embodiment of the present invention is substantially composed of step S0 of providing tea leaves as raw materials, step S1 of adding water to the tea leaves and allowing them to absorb the water, step S2 of steaming the tea leaves, step S3 of inoculating black koji mold into the steamed tea leaves, step S4 of culturing the black koji mold, and step S5 of obtaining a koji fermented composition.

(Preparation of Tea Leaves)

First, the step S0 of providing tea leaves shown in FIG. 1 will be described. The tea leaves used in the present invention do not only include the leaves of tea, but also include stems, branches and the like collected from tea trees. The tea leaves used as raw materials for the koji fermented composition of the present invention may not only be fresh tea leaves, but may also be tea leaves, which are subjected to a heat treatment immediately after they have been collected, or oolong tea or black tea, which is obtained by subjecting the collected tea leaves to oxidizing fermentation by oxidase contained in the fresh tea leaves, or further, post-fermented tea. Moreover, used tea leaves obtained after the brewing of such green tea, oolong tea, black tea or the like can also be used as tea leaves that are raw materials for the koji fermented composition of the present invention. In the present invention, green tea leaves, which are subjected to a heat treatment immediately after they have been collected, are preferably used, because the green tea is easily handled as a raw material and is not affected by oxidase contained in the fresh tea leaves in the subsequent step. Furthermore, in order to enhance efficiency in the subsequent steaming treatment or the subsequent culture of black koji mold, tea leaves or tea stems are preferably crushed to a certain size, which is not too large.

(Water Absorption Treatment)

Next, the water absorption treatment step S1 will be described. In the present step, a treatment of adding water to tea leaves or immersing the tea leaves in water, so that the tea leaves are allowed to absorb water, is carried out. The amount of water absorbed is adjusted, so that the water content of the tea leaves can be 20% to 60%, and preferably 30% to 50%. Specifically, for example, when dry green tea is used as raw material tea leaves, the amount of water absorbed can be determined based on the weight ratio of tea leaves.

(Streaming Treatment)

Next, the steaming treatment step S2 will be described. Tea leaves, which have been allowed to absorb water in the above described step, are placed in a steamer, the steamer is then covered, and water vapor is then applied to the tea leaves to heat them by heating the steamer. The time required for the steaming treatment is preferably approximately 30 minutes to 120 minutes, more preferably 45 minutes to 90 minutes, and particularly preferably approximately 60 minutes. By performing the present step, bacteria contained in the tea leaves are sterilized, and also, oxidase contained in the tea leaves is inactivated, so that black koji mold is allowed to efficiently proliferate in the tea leaves in the subsequent step. After completion of the steaming treatment, the tea leaves are removed from the steamer, are then spread uniformly on a board, and are then cooled to a temperature of approximately 30° C. to 40° C. Thereby, it becomes possible to inoculate koji mold into the tea leaves.

(Inoculation of Black Koji Mold)

Next, the step S3 of inoculating black koji mold into tea leaves will be described. In the present step, black koji mold is inoculated into the tea leaves, which have been cooled after completion of the above described steaming step. The term "black koji mold" is used in the present invention to mean a group of molds belonging to genus *Aspergillus*, which forms black or dark brown conidiospores (a form of asexual spores) used in the production of distilled spirits such as *Awamori* at Okinawa or imo shocyu (a distilled spirit made from sweet potato) at Kagoshima. Specific examples of such black koji mold include, but are not limited to, *Aspergillus awamori*, *Aspergillus saitoi*, *Aspergillus luchuensis*, *Aspergillus inuii*, *Aspergillus usami*, and *Aspergillus aureus*. In the present invention, from the viewpoint of achieving a significant effect of improving enzyme activity and reducing the amount of citric acid generated, *Aspergillus awamori*, *Aspergillus luchuensis*, *Aspergillus inuii*, and a combination thereof are preferable. Upon inoculation, black koji mold is uniformly dispersed on tea leaves spread on a board, so that the black koji mold can be inoculated into the tea leaves. At this time, the black koji mold is preferably inoculated into the tea leaves, such that 1,000,000 or more of black koji mold spores can be applied to 1 g of tea leaves as raw materials. For example, when the number of spores contained in 1 g of seed koji (seed malt) is two billion, approximately 1 g of the seed malt (0.1%) may be added to 1 kg of the tea leaves. After the black koji mold has been inoculated into the tea leaves, the black koji mold is preferably dispersed in the entire tea leaves by fully mixing the tea leaves.

(Culture)

Herein, the step S4 of culturing the black koji mold inoculated into the tea leaves will be described. In the present step, black koji mold is allowed to proliferate in tea leaves, into which the black koji mold has been inoculated. First, the tea leaves, in which the black koji mold has been dispersed, are placed in an incubation room, which is kept around 30° C. As time passes, fermentation progresses, and the temperature of the tea leaves is increased. However, since koji mold hardly grows if the temperature becomes higher than 40° C., air blow is carried out to decrease the temperature of the tea leaves, and the amount of air blow is adjusted such that the temperature of the tea leaves can be maintained at 30° C. to 42° C., and preferably at 30° C. to 40° C. Specifically, the temperature of the tea leaves is adjusted to be 35° C. to 40° C. by air blow for 12 to 30 hours after initiation of the culture, although the conditions are not limited thereto. Thereafter, the temperature of the tea leaves is adjusted to be relatively low (30° C. to 35° C.) by adjusting the amount of air blow, as described above, and a koji fermented composition is completed at a time point in which the culture is carried out for 1 to 4 days, preferably for 36 to 72 hours, and more preferably for 40 to 60 hours, in total from initiation of the culture.

It is to be noted that, in the koji fermented composition-producing steps S1 to S4, the washing of raw materials, water absorption, steaming, inoculation of koji mold, and koji culturing can be carried out by employing a machine capable of performing these operations in a single device (e.g., a drum-type automatic koji producing device, etc.).

(Koji Fermented Composition)

The obtained koji fermented composition is what is called "koji", in which black koji mold has proliferated in tea leaves. However, although such black koji mold has been allowed to proliferate, in the case of the koji fermented composition of the present invention, the amount of citric acid generated is reduced to less than half, and the acid protease activity and xylanase activity are enhanced, in comparison to ordinary malted rice or the like. Moreover, the koji fermented composition of the present invention has a high antioxidative activity, as in the case of the tea leaves of raw materials, but its cell growth inhibitory activity is low, differing from the tea leaves. The koji fermented composition obtained in the above described steps contains a certain amount of water. However, such water content can be removed by natural drying or low-temperature dehumidification drying. Furthermore, it is also possible to crush the koji fermented composition, from which the water content has been removed, to produce a powdery or granular koji fermented composition. Even if the water content has been once removed from the koji fermented composition, the function of the koji fermented composition can be effectively maintained.

The enhanced protease activity of the koji fermented composition of the present invention is an acid protease activity measured according to the method described in the National Tax Administration Agency Prescribed Analysis (the 4th Revision National Tax Administration Agency Prescribed Analysis, Brewing Society of Japan, 1993). When the enzyme titer is indicated as a value relative to dry matter, it is preferably 10,000 U/g koji or more, more preferably 20,000 U/g koji or more, and particularly preferably 30,000 U/g koji or more.

With regard to the xylanase activity of the koji fermented composition of the present invention, the amount of enzyme necessary for releasing 1 mg of xylose at 40° C. for 60 minutes according to the Somogyi-Nelson method is defined as 1 unit. When the enzyme titer is indicated as a value relative to dry matter, it is preferably 2 U/g koji or more, more preferably 5 U/g koji or more, and particularly preferably 8 U/g koji or more. The xylanase activity means an activity of hydrolyzing the β1,4-glycoside bond of xylan. It is not particularly limited, the xylanase activity in the present invention is measured as follows. First, standard solutions containing 0 to 240 μL/mL xylose are prepared, and 0.5 mL of each standard solution is colored according to the Somogyi-Nelson method. Thereafter, a standard curve is produced from the absorbance at 500 nm of colored standard solutions. On the other hand, 10 g of a sample, such as the koji fermented composition of the present invention, is extracted with 50 mL of an acetate buffer (pH 5), and is then filtrated. The filtrate is diluted with an acetate buffer (pH 3.7), as necessary. 0.4 mL of a 1% xylan solution serving as a substrate is added to 0.1 mL of the extract solution, and a reaction is then carried out at 40° C. for 60 minutes. Thereafter, 0.5 mL of the reaction solution is colored according to the Somogyi-Nelson method, the absorbance at 500 nm of colored solution is then obtained, and the free xylose concentration X (mg/tube) is then obtained from the standard curve. From this free xylose concentration X, the concentration of free xylose per g of sample can be calculated to obtain the xylanase activity.

Moreover, with regard to the reduced amount of citric acid, which is generated in the koji fermented composition of the present invention, when the acidity of the koji fermented composition is measured according to the aforementioned method of the National Tax Administration Agency Prescribed Analysis, the acidity value is preferably 10 mL or less, more preferably 8 mL or less, and particularly preferably 6 mL or less.

The koji fermented composition or its extract of the present invention can be used as a seasoning in food processing or food manufacturing. The term "seasoning" means a food additive used for the purpose of adding umami to food materials or food products. By applying the koji fermented composition of the present invention or an extract thereof to a food material, ingredients contained in the food material are degraded by enzymes contained in the koji fermented composition, and a sweet taste or umami can be added to the food material. The term "extract of the koji fermented composition" means beneficial ingredients such as various enzymes, which are separated from the koji fermented composition by dissolving the koji fermented composition in a solvent such as water or alcohol. In particular, since the koji fermented composition of the present invention has an enhanced acid protease activity, proteins contained in food materials are fully degraded, and amino acids constituting umami ingredients such as glutamic acid are obtained. Moreover, since the koji fermented composition of the present invention also has an enhanced xylanase activity, cell walls comprising hemicellulose as a main ingredient are easily degraded in plant food materials, and as a result, sweet tastes or umami ingredients can be eluted from the cell walls interior. As such, by sprinkling or putting the koji fermented composition of the present invention or an extract thereof on a food material, the umami taste of the food material can be easily increased, and thus, the food material can be processed to have a delicious taste. Furthermore, since the koji fermented composition of the present invention comprises sugars, amino acids, peptides and the like, which are derived from tea leaves, umami derived from the tea leaves can also be added to a food material. Further, by its enhanced enzymatic decomposition action, the koji fermented composition of the present invention is able to soften not only protein-containing food materials such as meats or fish meats, but also plant food materials.

When the koji fermented composition of the present invention or an extract thereof is used as a seasoning, the koji fermented composition or an extract thereof is mixed with another material, and it is used in the form of a mixture. Otherwise, the koji fermented composition or an extract thereof can also be used as one of raw materials for a seasoning. For example, water and salts are added to the koji fermented composition, and the mixture is then fermented at a room temperature for several days to obtain a shio-koji (salt-koji) seasoning using the koji fermented composition.

The koji fermented composition of the present invention or an extract thereof can be used as an antioxidant. The antioxidative activity of the koji fermented composition of the present invention means an action to suppress lipid peroxidation and an action to remove active oxygen species (e.g., superoxide anion, hydroxyl radical, singlet oxygen, etc.). An extract of the koji fermented composition means a beneficial ingredient having an antioxidative activity, which is separated from the koji fermented composition by dissolving the koji fermented composition in a solvent such as water or alcohol. Tea leaves have been conventionally known to have a high antioxidative activity. On the other hand, tea leaves also have a cell growth inhibitory activity. The koji fermented composition of the present invention has a high antioxidative activity, as with tea leaves, but its cell growth inhibitory activity is reduced, differing from tea leaves. Hence, for the purpose of preventing oxidation of contained ingredients, the koji fermented composition of the present invention can be widely used as a highly safe antioxidant in the fields of food products, medicines, cosmetics, etc.

The koji fermented composition of the present invention or an extract thereof can be used as a food product or beverage. Since the koji fermented composition of the present invention comprises the aforementioned enzymes and also has an antioxidative action, it can be preferably used as a medicine or a functional food based on these functions. The koji fermented composition or an extract thereof may be singly used as a food product or beverage, but it can also be used as one of raw materials for a food product or beverage. Otherwise, the koji fermented composition is added to another food material, and the obtained mixture is then fermented, so that another koji-fermented food product having the functions of the koji fermented composition of the present invention can be obtained.

Hereinafter, the present invention will be described in the following Examples. However, these examples are not intended to limit the scope of the present invention.

EXAMPLES

Example 1

1. Production of Koji Fermented Composition (Black Koji Mold-Based Malted Tea) by Using Black Koji Mold Water was added to 1 kg of commercially available green tea, and the water content of the green tea was adjusted to be in the range of 30% to 40%. Subsequently, the green tea was steamed in a steamer for 60 minutes, and was then cooled to 35° C. Thereafter, 1 g of black koji mold spores (two billion of spores/g) was uniformly dispersed on the green tea. *Aspergillus awamori* was used as such black koji mold, and the amount of black koji mold dispersed was adjusted to be 1,000,000 or more spores per gram of the green tea used as a raw material. After inoculation of the spores, the inoculated green tea was incubated at 35° C. and thus, a culture was carried out. As fermentation has progressed, the temperature of the fermented product was increased. Thus, for 24 hours after initiation of the culture, the temperature of the fermented product was adjusted to be 40° C. or lower by blowing air. Thereafter, the temperature of the fermented product was decreased to approximately 34° C. to 35° C. also by air blow, and the culture was further carried out for 16 hours, so as to obtain the koji fermented composition of the present invention (hereinafter referred to as "black koji mold-based malted tea").

Comparative Example 1

2. Production of Koji Fermented Composition by Using Yellow Koji Mold

The koji fermented composition of Comparative Example 1 (hereinafter referred to as "yellow koji mold-based malted tea") was obtained in the same manner as that of the above described Example 1, with the exception that *Aspergillus oryzae* (yellow koji mold) was used instead of *Aspergillus awamori* (black koji mold).

Comparative Example 2

3. Production of Black Koji Mold-Based Malted Rice by Using Black Koji Mold

The koji fermented composition of Comparative Example 2 (hereinafter referred to as "black koji mold-based malted rice") was obtained in the same manner as that of the above described Example 1, with the exception that white rice was used as a raw material, instead of green tea.

Comparative Example 3

4. Production of Yellow Koji Mold-Based Malted Rice by Using Yellow Koji Mold

The koji fermented composition of Comparative Example 3 (hereinafter referred to as "yellow koji mold-based malted rice") was obtained in the same manner as that of the above described Example 1, with the exceptions that white rice was used as a raw material, instead of green tea, and also that *Aspergillus oryzae* (yellow koji mold) was used instead of *Aspergillus awamori* (black koji mold).

Example 2

5. Measurement of Enzyme Activity and Citric Acid Amount in Koji Fermented Composition The black koji mold-based malted tea produced in Example 1 and each of koji fermented compositions produced in Comparative Examples 1 to 3 were measured in terms of the enzyme activities of acid protease and xylanase, and acidity. The enzyme activity of acid protease and the acidity were measured in accordance with the method described in the National Tax Administration Agency Prescribed Analysis (the 4th Revision National Tax Administration Agency Prescribed Analysis, Brewing Society of Japan, 1993). On the other hand, with regard to the xylanase activity, the amount of enzyme necessary for releasing 1 mg of xylose at 40° C. for 60 minutes according to the Somogyi-Nelson method was defined as 1 unit, and the enzyme activity was then measured by the above described method for measuring xylanase activity. The results are shown in FIGS. 2a to 2c. The enzyme titers of acid protease and xylanase were indicated as values on the basis of dry matter.

As shown in the graph of FIG. 2a, it was found that the black koji mold-based malted tea (malted tea/black koji) of the present invention has an acid protease activity that is 5 or more times higher than that of the black koji mold-based malted rice (malted rice/black koji). It was also demonstrated that the black koji mold-based malted tea (malted tea/black koji) of the present invention has an acid protease activity that is two or more times higher than that of the yellow koji mold-based malted tea (malted tea/yellow koji). Moreover, as shown in the graph of FIG. 2b, it was found that the black koji mold-based malted tea (malted tea/black koji) of the present invention has a xylanase activity that is 10 or more times higher than that of the black koji mold-based malted rice (malted rice/black koji). Since yellow koji mold originally does not produce xylanase, the value of xylanase activity of malted tea and malted rice using the yellow koji mold was 0 (zero). Furthermore, as shown in the graph of FIG. 2c, it was found that the acidity of the black koji mold-based malted tea (malted tea/black koji) of the present invention was reduced to substantially one third or less, in comparison to the black koji mold-based malted rice (malted rice/black koji). Since yellow koji mold originally does not produce citric acid, the acidity value of malted tea and malted rice using the yellow koji mold was 0 (zero). From these results, it was found that, by producing a koji fermented composition using tea leaves as raw materials and also using black koji mold as koji mold, the koji fermented composition, in which acid protease activity and xylanase activity are enhanced and the amount of citric acid generated is reduced, can be obtained.

Example 3

6. Confirmation of Umami-Enhancing Effect of Koji Fermented Composition

In order to confirm what influence the black koji mold-based malted tea of the present invention produced in Example 1 and each of koji fermented compositions produced in Comparative Examples 1 to 3 would have on food materials, the following test was carried out. First, koji fermented compositions produced in Example 1 and Comparative Examples 1 to 3 were each subjected to low-temperature dehumidification drying, so that they were processed in powdery koji fermented compositions. Subsequently, 30 mg of such each powdery koji was uniformly sprinkled on 100 g of a pork meat, and the pork meat was then left at rest in a refrigerator at 4° C. for 12 hours. Thereafter the pork meat was removed from the refrigerator, and the content of free glutamic acid in the pork meat was then quantified. Also, a pork meat, on which koji had not been sprinkled and no treatments had been performed, was also quantified in terms of the content of free glutamic acid. The results are shown in FIG. 3.

As shown in the graph of FIG. 3, it was found that protein ingredients contained in the meat are degraded and the amount of free glutamic acid is increased by sprinkling koji fermented composition on the meat. In particular, a pork meat, which had been treated with the black koji mold-based malted tea (malted tea/black koji) of the present invention, showed the largest amount of free glutamic acid, in comparison to the pork meats treated with the koji fermented compositions of other test groups. From these results, it was found that umami can be reliably enhanced by applying the black koji mold-based malted tea of the present invention to a food material, and that the black koji mold-based malted tea of the present invention is a seasoning capable of giving natural umami to food materials, because of its food material-derived ingredient.

From these Examples, it was found that when koji fermented composition is produced by using tea leaves as medium in which black koji mold proliferates, and by controlling temperature by blowing air, a koji fermented composition having a low acid taste and also having drastically improved acid protease activity and xylanase activity can be obtained.

Example 4

7. Measurement 1 of Antioxidative Activity of Koji Fermented Composition

Water was added to 1 kg of commercially available green tea, and the water content of the green tea was adjusted to be approximately 50%. This green tea was placed in a drum-type koji producing device, and was then subjected to a steaming treatment under conditions of 95° C. for 60 minutes. Thereafter, the tea leaves were cooled, and 1 g of spores of black koji mold (*Aspergillus awamori*) (two billion of spores/g) was added to and mixed with the tea leaves. Koji production was carried out in the drum-type koji producing device for 3 days, so as to obtain a koji fermented composition (hereinafter referred to as "malted tea"). The antioxidative activity of this malted tea was evaluated. As a control group, green tea (used as a raw material for the malted tea) was evaluated, and as other food product materials, garlic and white rice were also evaluated, in terms of antioxidative activity. Upon evaluation of the antioxidative activity, four types of tests, namely, (1) DPPH radical-scavenging activity, (2) superoxide anion radical-scavenging activity, (3) hydroxyl radical-scavenging activity, and (4) singlet oxygen-quenching activity, were carried out. Each test was carried out as follows.

(1) DPPH Radical-Scavenging Activity

Samples (malted tea, green tea, garlic, and white rice) were each extracted with 50% ethanol to obtain ethanol extracts. The extract of each sample was measured in terms of DPPH radical (DPPH.)-scavenging activity. That is, a 1.2 M 1,1-diphenyl-2-picrylhydrazyl (DPPH) solution was added to the extract, and the absorbance at 520 nm was then measured according to a 96-well microplate reader method. Using Trolox as a standard substance, the DPPH radical-scavenging activity was indicated in the form of the amount of Trolox Equivalent relative to 100 g of the sample (mg TE/100 g).

(2) Superoxide Anion Radical-Scavenging Activity

Samples (malted tea, green tea, garlic, and white rice) were added to ion exchange water at 90° C., and were then extracted under conditions of 90° C. for 5 minutes to obtain water extracts. Regarding the water extract of each sample, the superoxide anion radical ($O_2.^-$)-scavenging activity was measured according to an ESR spin trapping method. Superoxide anion radical ($O_2.^-$) was generated in a hypoxanthine/xanthine oxidase system, and as a spin trapping agent, DMPO (5,5-dimethyl-1-pyrroline-N-oxide) was used. The obtained spin adduct signals were detected using an electron spin resonance apparatus (JES-FA100, manufactured by JEOL Ltd.). A superoxide dismutase (SOD) standard was used to prepare a calibration curve, and based on the calibration curve, the superoxide-scavenging activity was indicated in the form of SOD-like activity (units SOD/g) relative to 1 g of the sample.

(3) Hydroxyl Radical-Scavenging Activity

Samples (malted tea, green tea, garlic, and white rice) were added to ion exchange water at 90° C., and were then extracted under conditions of 90° C. for 5 minutes to obtain water extracts. Regarding the water extract of each sample, the hydroxyl radical (.OH)-scavenging activity was measured according to an ESR spin trapping method. That is, 50 μL of the extract, 75 μL of a 0.1 mM ferrous sulfate solution comprising 0.55 mM diethylenetriaminepentaacetic acid (DTPA), 75 μL of a 1 mM hydrogen peroxide solution, and 20 μL of a 8.8 mM DMPO solution were mixed with one another, and immediately after the mixing, signals were detected in the mixed solution, using an electron spin resonance apparatus (JES-FA100, manufactured by JEOL Ltd.). Dimethyl sulfoxide (DMSO) serving as a scavenger of hydroxyl radicals was used to prepare a calibration curve, and based on the calibration curve, the hydroxyl radical-scavenging activity was indicated in the form of DMSO-like activity (μmol DMSO/g) relative to 1 g of the sample.

(4) Singlet Oxygen-Quenching Activity

Samples (malted tea, green tea, garlic, and white rice) were added to ion exchange water at 90° C., and were then extracted under conditions of 90° C. for 5 minutes to obtain water extracts. Regarding the water extract of each sample, the singlet oxygen ($^1O_2$)-quenching activity was measured according to an ESR spin trapping method. That is, 40 μL of the extract, 40 μL of 1 mM 2-amino-4(1H)-pteridinone (pterine), 40 μL of 100 mM 2,2,6,6-tetramethyl-4-piperidone (TMPD), 20 μL of 15 mM diethylenetriaminepentaacetic acid (DTPA), and 60 μL of 100 mM phosphate buffer (pH 7.4) were mixed with one another, and the mixed solution was then exposed to ultraviolet ray for 40 seconds. Thereafter, signals were then measured using an electron spin resonance apparatus (JES-FA100, manufactured by JEOL Ltd.). Histidine serving as a scavenger of singlet oxygen was used to produce a calibration curve, and based on the calibration curve, the singlet oxygen-quenching activity was indicated in the form of histidine-like activity (μmol histidine/g) relative to 1 g of the sample.

The results of the antioxidative activity tests are shown in FIGS. 4 to 7. It was found that malted tea comprising the koji fermented composition of the present invention has a high antioxidative action, in comparison to other food products such as garlic or white rice. In addition, as conventionally known, green tea has been known to comprise catechins and vitamins and to have a high antioxidative action. It was demonstrated that the koji fermented composition of the present invention (malted tea) exhibits an extremely high antioxidative activity, that the present koji fermented composition has a DPPH radical-scavenging activity that is 1.35 times higher than that of green tea (FIG. 4) and has a superoxide-scavenging activity that is a half of that of green tea (FIG. 5), and that the hydroxyl radical-scavenging activity (FIG. 6) and singlet oxygen-quenching activity (FIG. 7) of the present koji fermented composition are 60% or more of that of green tea.

Example 5

8. Measurement 2 of Antioxidative Activity of Koji Fermented Composition

Three types of samples, namely, the malted tea (koji fermented composition) produced in Example 4, green tea used as a raw material for the malted tea, and bovine serum albumin (BSA) were subjected to a thiobarbituric acid reactive substance (TBARS) test for quantifying lipid peroxidation of cells, and their antioxidative activity was evaluated. The test was carried out as follows.

10 g of the malted tea produced in Example 4 was added to 500 mL of ion exchange water at 90° C., and was then extracted under conditions of 90° C. for 5 minutes. The extract was filtrated with a filter paper No. 2. The filtrate was concentrated using a rotary evaporator, and was then subjected to vacuum drying to prepare powders, thereby obtaining a malted tea extract. Regarding a green tea extract, instead of the above described malted tea, 10 g of green tea, which had been used as a raw material for the malted tea, was extracted with ion exchange water, and was then subjected to concentration and drying treatments in the same manner as described above, to obtain it in the form of powders.

Mouse myoblasts C2C12 cells were inoculated onto a petri dish, and then, were allowed to grow therein and were differentiated into myotube cells. The above described malted tea extract, green tea extract, and bovine serum albumin were each added in a concentration of 0.1% to a medium, and were then cultured for 48 hours. Each culture solution was subjected to a TBARS test, and the amount of TBARS was measured. Moreover, the total protein content of the cells in each culture solution was measured by a Bradford method. Specifically, 500 μL of the culture solution obtained 48 hours after initiation of the culture was collected with a microtube, and 1000 μL of 5-fold dilution protein assay staining solution (manufactured by Bio-Rad Laboratories) was then added to and mixed with the culture solution. The obtained mixture was left at a room temperature for 15 minutes, and the absorbance at 595 nm was then measured. Based on a standard curve for bovine serum albumin, the total protein content was calculated. From the value of TBARS and the value of total protein content, the concentration of TBARS per mg of cell-derived protein in each culture solution (TBARS MDA nmol/mg) was obtained.

Furthermore, using ferric nitrilotriacetate (Fe-NTA), oxidative stress was induced to a test sample, and the antioxidative activity of the test sample was then measured. Specifically, in the above described TBARS test method, when a test sample such as a malted tea extract was added to a medium, ferric nitrilotriacetate for inducing oxidative stress was also added thereto, and the obtained mixture was then cultured for 48 hours. Forty-eight hours later, each culture solution was subjected to the TBARS test, and the total protein content thereof was measured, so that the TBARS concentration was obtained.

The results are shown in the graph of FIG. 8. The longitudinal axis indicates the concentration of TBARS per mg of cell-derived protein in each culture solution (TBARS MDA nmol/mg). The bar "not added" (white) indicates the value of a group to which ferric nitrilotriacetate has not been added, whereas the bar "Fe-NTA added" (black) indicates the value of a group to which ferric nitrilotriacetate for inducing oxidative stress has been added. From these results, it was found that the TBARS values were reduced by addition of malted tea in all groups, and that the lipid peroxide reaction was suppressed. Moreover, even comparing with the value of green tea having a high antioxidative activity, the TBARS value was reduced, and thus, it was confirmed that the malted tea comprising the koji fermented composition of the present invention has a high antioxidative action.

The total protein contents (Fe-NTA not added) of cells in each of culture solutions, which were measured by the test of the present example, are shown in the graph of FIG. 9. The longitudinal axis indicates the total protein content of cells in a petri dish, to which the culture solution has been added. From these results, it was found that the protein content of cells was significantly reduced at a level of significance of 5% or less by adding a green tea extract to a medium. This suggests that the green tea have an action to inhibit cell growth. On the other hand, in the case of malted tea obtained by fermenting green tea with black koji mold, it was found that the cell growth inhibitory action as possessed by green tea was significantly reduced, and that almost no cell growth inhibitory action was observed and the malted tea would have only a small effect on cell growth.

From these test results, it was found that, by fermenting tea leaves and making koji, the antioxidative activity of the tea can be maintained, while the cell growth inhibitory action of the tea is suppressed. Thereby, it was demonstrated that the koji fermented composition of the present invention can be utilized as a food-derived highly safe antioxidant in the fields of food products, medicines, etc.

The present invention is not limited to the above described embodiments or examples. Various modifications are included in the technical scope of the present invention, as long as they do not deviate from the gist of the invention described in the claims.

INDUSTRIAL APPLICABILITY

The koji fermented composition of the present invention cannot only be utilized as a seasoning or an antioxidant, but it can also be utilized in the field of food products, food processing, food manufacturing, and medicines.

The invention claimed is:

1. A method for producing an antioxidant, which comprises the steps of inoculating *Aspergillus awamori* into tea leaves, and culturing the tea leaves for 36 to 72 hours in total, wherein the culture of tea leaves in the culture step is carried out by adjusting the temperature of the tea leaves at 35° C. to 40° C. for 12 to 30 hours after initiation of the culture, and then, at 30° C. to 35° C., and wherein the antioxidant comprises DPPH radical-scavenging activity.

2. A method for producing a seasoning, comprising the steps of inoculating *Aspergillus awamori* into tea leaves and culturing the tea leaves for 36 to 72 hours in total, wherein the culture of the tea leaves in the culture step is carried out by adjusting the temperature of the tea leaves at 35° C. to 40° C. for 12 to 30 hours after initiation of the culture, and then at 30° C. to 35° C.

* * * * *